United States Patent [19]

Pennington et al.

[11] Patent Number: 4,885,412

[45] Date of Patent: Dec. 5, 1989

[54] ALDEHYDE PRODUCTION FROM ALKYLAROMATICS USING MOLTEN NITRATE SALT CATALYST

[75] Inventors: B. Timothy Pennington, Sulphur, La.; Lawrence E. Katz, Orange, Conn.

[73] Assignee: Olin Corporation, Cheshire, Conn.

[21] Appl. No.: 255,238

[22] Filed: Oct. 11, 1988

[51] Int. Cl.$^4$ .................. C07C 27/12; C07C 45/32
[52] U.S. Cl. ......................... 568/469.9; 568/470
[58] Field of Search ..................... 568/469.9, 470

[56] References Cited

U.S. PATENT DOCUMENTS

| | | | |
|---|---|---|---|
| 3,641,572 | 2/1972 | Riegel et al. | 568/469.9 |
| 3,869,518 | 3/1975 | Sze et al. | 568/469.9 |
| 3,939,209 | 2/1976 | Sze et al. | 568/469.9 |

FOREIGN PATENT DOCUMENTS 0268870  6/1988  European Pat. Off. ............ 568/470

*Primary Examiner*—Werren B. Lone
*Attorney, Agent, or Firm*—Dale Lynn Carlson

[57] ABSTRACT

A process for producing aldehydes and, more specifically, a process employing a vapor phase reaction in the presence of a molten nitrate salt catalyst.

10 Claims, No Drawings

ALDEHYDE PRODUCTION FROM ALKYLAROMATICS USING MOLTEN NITRATE SALT CATALYST

FIELD OF THE INVENTION

This invention relates generally to a process for producing aldehydes and, more specifically, to a process employing a vapor phase reaction in the presence of a molten nitrate salt catalyst.

BACKGROUND OF THE INVENTION

The production of aldehydes from hydrocarbons is known in the art, but in general, such production requires an expensive starting material or the initial production of intermediates. Thus, for example, in producing acetaldehyde from a hydrocarbon, the starting material is generally ethylene, an expensive starting material. In the production, for example, of benzaldehyde, the starting material can be toluene, but the toluene generally then must be converted to a chlorosubstituted intermediate which is subsequently converted to benzaldehyde.

Three patents, all assigned to the Lummus Company, disclose processes for preparing aldehydes by reacting an alkane with an oxygen-containing gas in a molten mixture of the higher and lower valent forms of a multivalent metal chloride. U.S. Pat. No. 3,641,157 discloses such a reaction generally, whereas U.S. Pat. Nos. 3,869,518 and 3,939,209 focus more specifically on the production of acetaldehyde from ethane in such a molten metal chloride mixture. Unfortunately, the use of these molten metal chlorides is highly undesirable due to the corrosiveness of the materials. Moreover, the selectivity to aldehyde production of such a process is less than might be desired, as detailed in the comparative working examples given hereinbelow.

Accordingly, it would be highly desirable to provide a new process for producing aldehydes which is simple, direct and does not suffer from the abovementioned corrosiveness problem. In addition, it would be highly desirable to provide a process that offers excellent selectivity to the desired aldehyde.

SUMMARY OF THE INVENTION

The present invention relates to a process for producing an aldehyde or mixture of aldehydes by a reaction which comprises reacting an alkylaromatic compound having from 7 to 22 carbon atoms per molecule, or mixture thereof, with an oxygen-containing gas, said alkylaromatic compound and said oxygen-containing gas being gaseous reactants, by contacting said gaseous reactants with a bath, stream, spray or mist of at least one molten nitrate salt catalyst, said catalyst being present in an amount sufficient to absorb any heat generated during said reaction while maintaining an essentially constant reaction temperature, said reaction being conducted at a reaction temperature of between about 135° C. and about 600° C. and a reaction pressure of between about 1 and about 50 atmospheres.

DETAILED DESCRIPTION OF INVENTION

Several factors will affect the reactant conversion to aldehyde and the selectivity of aldehyde production vis-a-vis by-product production in accordance with the process of the present invention. These factors include, for example: the contact time of the molten salt with the oxygen-containing gas, the temperature of the reactor product gases, the molten salt temperature, the molten salt catalyst composition, the feed gas temperature, the feed gas composition, the feed gas pressure, and the co-catalyst employed (if any).

The oxygen-containing gas useful as a reactant in the present invention can be any such gas. Typically, air is employed as the oxygen-containing gas based upon its ready availability. However, other oxygen-containing gases such as pure oxygen may be employed if desired, and the use of oxygen is expected to be preferred in a commercial setting.

The alkylaromatic compound useful in the present invention generally has from 7 to 22 carbon atoms per molecule, preferably from 7 to 15 carbon atoms, more preferably from 7 to 12 carbon atoms, most preferably from 7 to 8 carbon atoms. Typical alkylaromatics include toluene, chlorotoluene, methoxytoluene, ethoxytoluene, ethylbenzene, xylenes, cumene, mesitylene and styrene.

The alkylaromatic reactant is preferably preheated to prevent condensation in the line delivering this gas to the reactor. Alternatively, both the oxygen-containing gas and the alkylaromatic vapor (collectively referred to herein as "the feed gases") can be preheated to prevent condensation in any of the feed lines. However, in the absence of preheat, the molten nitrate salt will rapidly heat the feed gases up to reaction temperature. If the feed gas is preheated, it preferably is maintained at at least about 100° C. in the feed gas line(s).

The molten nitrate salt(s) catalyst is generally maintained at a temperature sufficient to keep the salt(s) in a molten condition. Preferably, the temperature is maintained between about 135° C. (275° F.) and about 600° C. (1,000° F.), more preferably between about 200° C. and about 600° C., most preferably between about 250° C. and about 550° C. during the reaction in accordance with the present invention, and conveniently about 135° C. to about 450° C.

The specific temperature selected is based upon the melting point of the particular molten nitrate salt chosen. For example, mixtures of molten lithium nitrate and potassium nitrate can be suitably employed at a temperature as low as about 280° F., and hence, this temperature may be employed when using lithium nitrate. In the selection of a suitable molten nitrate salt bath temperature, it is important to choose a temperature below the thermal decomposition temperature for the particular molten nitrate salt chosen. In addition, it is important to maintain a sufficient isotherm across the molten nitrate salt bath so as to avoid crust formation of the nitrate salt in the bath. Such a crust formation in the nitrate salt bath can cause localized overheating of gases trapped by the crust in the bath and an associated "runaway" oxidation reaction due to overheating of the gases in the bath. In order to maintain a bath isotherm, constant stirring of the molten nitrate salt bath is preferred. Alternatively, the molten salt can be circulated by conventional means, such as the use of internal draft tubes or external pumping loops.

The nitrate salt catalyst used may be any one of the alkali or alkaline earth nitrates such as lithium, sodium, potassium, rubidium, cesium, magnesium, calcium, strontium, or barium or mixtures thereof. In addition, the nitrate salts can be used in mixtures with other salts such as chlorides, bromides, carbonates, sulfates, and phosphates. Generally, the content of the other salt(s), when present, should be restricted to less than 60 percent by weight based upon the weight of the total melt and in most cases their contents should not exceed about 25 percent of the total melt.

The ratio of alkylaromatic compound to oxygen in the oxygen-containing gas in the reactor can vary over a wide range. However, in accordance with the present invention, it has now been found that enhanced selectivity of aldehyde product is achieved by maintaining a relatively low amount of oxygen relative to the amount of alkylaromatic fed into the reactor. For example, when reacting toluene with oxygen in a molten potassium nitrate salt column at atmospheric pressure, a ratio of between about 1:5 and about 1:25 volume percent of oxygen to the reactant, e.g., about 5 volume percent oxygen to about 95 volume percent toluene is expected to provide an enhanced selectivity of benzaldehyde. When using air as the oxygen-containing gas, it is preferably employed in an amount of between about 5 and about 75 volume percent based upon the total amount of air plus alkylaromatic employed in the reaction.

In the selection of the ratio of the volume of oxygen-containing gas relative to the volume of alkylaromatic employed in the reaction mixture, the range of ratios which might pose a flammability hazard should be avoided, as is well known. For example, when utilizing an air/toluene reactant mixture at atmospheric pressure, the range of between about 1.2 and about 7.1 volume percent of toluene based upon total air plus toluene should be avoided.

A co-catalyst can also be used in accordance with the present invention. It is envisioned that an elemental metal, or the oxide or hydroxide thereof, when employed as a co-catalyst in conjunction with the molten nitrate salt catalyst, makes it possible to lower the reaction temperature for the particular nitrate salt selected and/or enhance the selectivity or conversion to the desired aldehyde. For example, a palladium or alumina or a silver co-catalyst such as silver nitrate, or a molybdenum oxide co-catalyst is expected to reduce the required reaction temperatures. The use of these metal co-catalysts are preferred when the reaction is conducted at atmospheric pressure. At superatmospheric pressure, an alkali metal hydroxide co-catalyst, such as sodium hydroxide, is believed to be particularly advantageous in providing enhanced selectivity to the desired product. In addition, in a continuous process employing caustic recycle, the alkali metal hydroxide is expected to enhance the desired product distribution by removing by-product carbon dioxide by forming alkali metal carbonate.

The co-catalyst (if used) is generally employed in a catalytically effective amount, generally in an amount of less than about 5 (preferably between about 0.5 and about 5, more preferably in an amount between about 0.5 and about 3) weight percent based on the total amount of co-catalyst plus molten salt catalyst.

The molten salt catalyst in which the co-catalyst (if used) is suspended or dispersed, helps to maintain the co-catalyst at a constant desired temperature or isotherm. The maintenance of the co-catalyst in such an isotherm makes it possible to reduce or avoid the problems of co-catalyst de-activation that might otherwise be encountered in a non-isothermal system due to overheating of the co-catalyst itself or due to thermal degradation of product to a tarry by-product which can coat, and thus de-activate, the catalyst.

Typically, the molten salt(s) is employed in an amount on a weight basis of between about 5 times and about 100 times (preferably between about 5 times and about 50 times) the total weight of the reactants employed.

The molten salt(s), in addition to functioning as a catalyst and as an isothermal medium for any co-catalyst, also serve as a temperature regulator. More specifically, the molten nitrate salt(s) have a high heat absorption capacity, enabling them to absorb large quantities of heat during the exothermic oxidation reaction while maintaining an essentially constant reaction temperature and thereby preventing a runaway reaction. The absorbed heat of reaction from this exothermic oxidation may be employed in the process of the present invention to help maintain the molten salt in a molten state and/or to heat the gaseous reactants to reaction temperature.

In a preferred embodiment of the present invention, a mixture of potassium and sodium molten nitrate salts is employed comprising between about 20 and about 80 weight percent of sodium nitrate, preferably between about 45 and about 65 weight percent of sodium nitrate based upon the total amount of sodium nitrate and potassium nitrate in the molten salt mixture. Another preferred molten mixture is a mixture of sodium nitrate, lithium nitrate, and potassium nitrate salts, preferably in a ratio of between about 10 and about 30 weight percent of lithium nitrate and between about 15 an about 75 weight percent of sodium nitrate based on the total amount of the mixture.

One method of contacting the gaseous reactants in the presence of the molten nitrate salt is by bubbling the reactants through a bath of the molten salt. If the gaseous reactants are bubbled into the bottom of the bath or column containing the molten nitrate salt, the contact time of the reactants with the molten salt catalyst is equal to the "rise time" of the reactants through the bath or column. Thus, the contact time can be increased by increasing the length of the molten nitrate salt bath or column. An alternate method of contacting the gaseous reactants in the presence of the molten salt would be to pass the gaseous reactants through a reactor countercurrently to a spray or mist of the molten salt. This latter method provides for enhanced surface area contact of the reactants with the molten salt. Still another method of contacting the gaseous reactants with molten salt would be to inject the reactants into a circulating stream of molten salt, wherein the kinetic energy of both streams is utilized to provide intimate mixing through the application of nozzles, mixers, and other conventional equipment. This latter method is expected to be preferred in a commercial setting. These methods are only illustrative of types of reaction systems which may be employed in the practice of this disclosure. Other conventional methods of gas-liquid contact in reaction systems may also be employed.

The alkylaromatic feed gas(es) can be passed into the molten nitrate salt-containing reactor using a separate stream (e.g. feed tube) from the stream delivering the oxygen-containing gas to the reactor. Alternatively, the reactant gases can be fed into the reactor together in a single stream. In a preferred embodiment of the present invention, two co-axially mounted feed gas tubes are employed. The co-axial mounting of the feed gas tubes has been found to reduce or minimize the back-up of molten salt into an unpressurized feed tube if pressure is temporarily lost in either (but not both) feed tube. Mixing of the gaseous reactants prior to, or at the point of, the gas(es) inlet into the reactor is desired in order to facilitate the oxidation reaction. Mixing is suitably accomplished using an impingement mixer or sparger tube.

If a bath of molten salt is employed, the feed gas is preferably bubbled into the molten nitrate salt-containing reactor using a sparger. If used, the sparger is preferably positioned in the molten nitrate salt to a sparger exit port depth of between about 2 and about 1000 centimeters, preferably between about 10 and about 200 centimeters, depending upon the size of the reactor utilized and the overall depth of the molten salt in the reactor. Alternatively, the gas can be fed directly into the bottom of the reactor by a feed tube. The feed gas tubes are preferably co-axially mounted so that in the event of a loss of pressure in either gas tube, the gas in the other tube will maintain sufficient pressure to keep the molten salt from backing up into the unpressurized feed gas tube.

This process can be run in a batchwise or continuous operation, the latter being preferred. The order of introduction of the reactants is determined by the operator based on what is most safe and practical under prevailing conditions. Generally, the desirability of avoiding flammable gas mixtures throughout the reaction and subsequent product separation systems will dictate the desired procedures.

The process can be carried out by feeding a mixture of aromatic, inert gas, and oxygen into a reaction vessel containing molten nitrate salt. The reaction vessel can be glass, glass-lined metal, or made of titanium. For example, a stainless steel autoclave 10 can be used, although, even better from a commercial point of view, is an unlined type 316 stainless steel autoclave (as defined by the American Iron and Steel Institute). A tubular reactor made of similar materials can also be used together with multi-point injection to maintain a particular ratio of reactants. Other specialized materials may be economically preferred to minimize corrosion and contamination of the molten salt and products, or to extend the useful life of the reaction system.

Some form of agitation of the molten salt(s)/feed gas mixture is preferred to avoid a static system and insure the homogeneity of the molten salt, agitation helps prevent crust formation of the salt(s) at the head gas/salt interface in the reactor. This can be accomplished by using a mechanically stirred autoclave, a multi-point injection system, or a continuous process, e.g., with a loop reactor wherein the reactants are force circulated through the system. Sparging can also be used. In the subject process, it is found that increased rates of reaction are obtained by good gas-liquid contact provided by agitation of the molten salt/gas mixture.

The process of the present invention is suitably carried out at atmospheric, subatmospheric or superatmospheric pressure. Typically, the process is effected at superatmospheric pressures of up to about 100 atmospheres, preferably between about 1 atmosphere and about 50 atmospheres, more preferably between about 1 atmosphere and about 35 atmospheres. The most preferred pressure range is between about 1 and about 25 atmospheres.

It is to be understood that by-products are also produced during the reaction. For example, some fragmentation and dehydrogenation of the alkylaromatic 10 feed is also effected, particularly at higher temperatures within the hereinabove noted temperature range, and therefore, the reaction conditions are generally controlled to minimize such production. The separation of the resulting by-products in order to recover the desired product may be effected by a wide variety of well-known procedures such as: absorption in water followed by fractional distillation, absorption, and condensation.

The following examples are intended to illustrate, but in no way limit the scope of, the present invention.

EXAMPLE 1

Benzaldehyde Production at Atmospheric Pressure in a Molten Nitrate Mixture

Liquid toluene at the rate of 0.08 cc/min was injected into a gas stream consisting of 500 cc/min nitrogen and 400 cc/min air. This gas stream at slightly above atmospheric pressure containing the injected toluene was sparged through a stirred molten salt reactor with a molten salt bed about 55 cm in depth and 9 cm in diameter. The molten salt was composed of 5500 grams of sodium nitrate and 4500 grams of potassium nitrate at 455° C. The gases exiting the reactor were cooled in a dry ice-isopropanol trap to remove condensible substances and then were allowed to flow through a sample vessel. After two hours operation, the reaction feed stream was shut off and the contents of the trap and gas sample vessel were analyzed. The trap contained 4.1 ml of liquid which was 99.3 percent unreacted toluene, 0.5 percent benzaldehyde, and 0.2 percent benzene. The gas sample contained the reaction products carbon dioxide, benzene, and benzaldehyde. No other reaction products were found. The toluene conversion was about 0.7 percent, selectivity to benzaldehyde was 71 percent, and the selectivity to the dealkylation product benzene was 29 percent.

EXAMPLE 2

Another Example of Benzaldehdye Production at Atmospheric Pressure in a Molten Nitrate Salt Mixture Another trial was carried out as in EXAMPLE 1 except that the toluene was carried into the reactor from a vaporizer apparatus so that the toluene comprised about 1 percent of the feed gas with the rest being air. Also, the molten salt temperature was raised to 482° C. and the reaction was continued for eight hours with a feed gas flow through rate of 500 cc/min. The toluene single pass conversion was found to be 3.8 percent. Selectivities to benzaldehyde and benzene were found to be 84 and 16 percent, respectively.

EXAMPLE 3

4-Chlorobenzaldehyde Production at Atmospheric Pressure in a Molten Nitrate Mixture The compound 4-chlorotoluene was oxidized to 4-chlorobenzaldehyde in a manner similar to EXAMPLE 2. At 482° C., the conversion to products was 4.9 percent and the selectivities to 4-chlorobenzaldehyde, chlorobenzene, and toluene were 91.1, 8.8, and 0.1 percent, respectively. At 450° C. the conversion was 2.05 percent and the selectivities to 4-chlorobenzaldehyde and chlorobenzene were 95.8 and 4.2 percent, respectively.

EXAMPLE 4

Anisaldehyde Production at Atmospheric Pressure in a Molten Nitrate Salt Mixture The compound 4-methoxytoluene was oxidized to anisaldehyde in a manner similar to the procedure followed for EXAMPLE 2. At 450° C. the conversion to products was 1.2 percent and the selectivities to anisaldehyde and anisole were 94.2 and 5.8 percent, respectively.

EXAMPLE 5

Toluene Oxidation at Higher Than Atmospheric Pressure in a Molten Nitrate Salt Mixture Another trial was carried out as in EXAMPLE 2 using toluene and air but with the air fed in at 150 psig and a total gas flow rate of 2000 cc/min. The mixture of about 1 percent toluene and air was sparged through the molten nitrate salt mixture at 450° C. for one hour at the reaction pressure of 150 psig. Analysis showed the toluene conversion to be 0.8 percent with a selectivity to benzene of 7.9 percent and to benzaldehyde of 91.3 percent.

COMPARATIVE EXAMPLE A

Benzaldehyde Production at Atmospheric Pressure in a Molten Chloride Salt Mixture Another trial was carried out using toluene as in EXAMPLE 2 except that the molten salt mixture consisted of 40 weight percent of cuprous chloride, 30 weight percent of cupric chloride, and 30 weight percent potassium chloride. The molten chloride salt temperature was held at 462° C. and the toluene air mixture was sparged through the salt bed for two hours at a feed gas flow rate of 1000 cc/min total flow. The feed gas contained about 1 percent toluene. Analysis showed that the toluene single pass conversion was 0.7 percent. Also present were two products not seen when the molten salt mixture consisted of molten sodium nitrate and potassium nitrate. These two products were mesitylene and benzyl alcohol. The product selectivities were calculated to be 11.2 percent to benzene, 6.9 percent to mesitylene, 43.5 percent to benzaldehyde, and 38.4 percent to benzyl alcohol.

What is claimed is:

1. A process for producing an aldehyde or mixture of aldehydes by a reaction which comprises reacting an alkylaromatic compound selected from the group consisting of toluene, chlorotoluene, methoxytoluene, ethoxytoluene, ethylbenzene, xylenes, cumene, mesitylene and styrene, or mixture thereof, with an oxygen-containing gas, said alkylaromatic compound and said oxygen-containing gas being gaseous reactants, by contacting said gaseous reactants with a bath, stream, spray or mist of at least one alkali metal or alkaline earth metal molten nitrate salt catalyst, said catalyst being present in an amount sufficient to absorb any heat generated during said reaction while maintaining an essentially constant reaction temperature, said reaction being conducted at a reaction temperature of between about 135° C. and about 600° C. and a reaction pressure of between about 1 and about 50 atmospheres to produce the aldehyde or mixture of aldehydes.

2. The process of claim 1 wherein said reaction provides a molar selectivity to aldehyde formation of greater than 85 percent based upon said alkylaromatic.

3. The process of claim 2 wherein said selectivity is at least 90 percent.

4. The process of claim 1 wherein said molten salt comprises a mixture of sodium nitrate and potassium nitrate.

5. The process of claim 1 wherein said molten salt comprises a mixture of sodium nitrate, potassium nitrate and lithium nitrate.

6. A process for producing an aldehyde or mixture of aldehydes by a reaction which comprises reacting an alkylaromatic compound selected from the group consisting of toluene, chlorotoluene, methoxytoluene, ethoxytoluene, ethylbenzene, xylenes, cumene, mesitylene and styrene, or mixture thereof, with an oxygen-containing gas, said alkylaromatic compound and said oxygen-containing gas being gaseous reactants, by contacting said gaseous reactants with a bath, stream, spray or mist of at least one alkali metal or alkaline earth metal molten nitrate salt catalyst, said catalyst being present in an amount sufficient to absorb any heat generated during said reaction while maintaining an essentially constant reaction temperature, said reaction being conducted at a reaction temperature of between about 135° C. and about 450° C. and a reaction pressure of between about 1 and about 25 atmospheres to produce the aldehyde or mixture of aldehydes.

7. The process of claim 6 wherein said reaction provides a molar selectivity to aldehyde formation of greater than 85 percent based upon said alkylaromatic.

8. The process of claim 7 wherein said selectivity is at least 90 percent.

9. The process of claim 6 wherein molten salt comprises a mixture of sodium nitrate and potassium nitrate.

10. The process of claim 6 wherein molten salt comprises a mixture of sodium nitrate, potassium nitrate, and lithium nitrate.

* * * * *